US005852667A

United States Patent [19]
[11] Patent Number: 5,852,667
[45] Date of Patent: Dec. 22, 1998

Pan et al.

[54] DIGITAL FEED-FORWARD ACTIVE NOISE CONTROL SYSTEM

[76] Inventors: Jianhua Pan, 401-1396 Ogilvie Road, Gloucester, Ontario, Canada, K1J 8V8; Anthony J. Brammer, 4792, Massey Lane, Gloucester, Ontario, Canada, K1J 8W9

[21] Appl. No.: 673,459

[22] Filed: Jul. 1, 1996

Related U.S. Application Data

[60] Provisional application No. 60/000,834, Mar. 7, 1995.

[51] Int. Cl.[6] ........ A61F 11/06

[52] U.S. Cl. ........ 381/71.1; 381/71.5; 381/71.6; 381/71.11

[58] Field of Search ........ 381/71, 94, 71.1, 381/71.5, 71.6, 71.7, 71.8, 71.11, 71.12, 158–159

[56] References Cited

U.S. PATENT DOCUMENTS

| | | | |
|---|---|---|---|
| 5,018,202 | 5/1991 | Takahashi et al. | 381/71 |
| 5,156,153 | 10/1992 | Bonnefous . | |
| 5,267,320 | 11/1993 | Fukumizu . | |
| 5,311,453 | 5/1994 | Denenberg et al. . | |
| 5,410,605 | 4/1995 | Sawada et al. | 381/71 |
| 5,548,543 | 8/1996 | Wang | 364/724.16 |

FOREIGN PATENT DOCUMENTS

| | | |
|---|---|---|
| 192379 | 2/1986 | European Pat. Off. . |
| 471290 | 8/1991 | European Pat. Off. . |
| 71999962 | 8/1995 | Japan . |

*Primary Examiner*—Forester W. Isen
*Assistant Examiner*—Duc Nguyen

[57] ABSTRACT

A method of noise control of an acoustic signal comprising: obtaining a reference signal of the acoustic signal to be controlled, applying an antinoise signal to the acoustic signal so as to control the acoustic signal, obtaining an error signal resulting from the application of the antinoise signal to the acoustic signal, generating the antinoise signal from the reference signal by passing the reference signal through a first filter having controllable filter coefficients, using a simplified model of a signal path from a location of the antinoise signal to a location of the error signal to obtain a modified representation of the reference signal, controlling the first filter coefficients by processing the error signal and the modified representation of the reference signal and generating a coefficient control signal such as to generate the antinoise signal, and applying the coefficient control signal to the first filter.

32 Claims, 9 Drawing Sheets

DIGITAL FEED-FORWARD ACTIVE NOISE CONTROL SYSTEM

This application is a continuation of Provisional Application No. 60/000,834, filed Mar. 7, 1995.

FIELD OF THE INVENTION

This invention relates to the field of sound controllers, and in particular to an adaptive feed-forward active noise control method.

BACKGROUND TO THE INVENTION

Noise control, and particularly active noise reduction, has been an objective for many years, particularly to reduce the ambient noise in airplanes or in industrial environments. Such systems have generally utilized feeding a canceling sound (referred to as anti-noise hereinafter) in inverse phase to a sound that is to be reduced or eliminated. Systems have been designed which are comprised of open loop control systems or closed loop control systems, analog or digital, the anti-noise being applied in a feedback or in a feedforward system.

Much of the progress in this field has been directed to the control of noise in a duct, such as an air conditioning duct or an automotive exhaust pipe. However, there has also been a need to control noise in an earcup, such as would be used by a helicopter pilot.

One of the early noise control systems directed to control of noise in an earcup is described in U.S. Pat. No. 2,972,018, invented by M. E. Hawley et al. This patent describes the use of a microphone which picks up sound to be canceled, close to the exterior of an earcup, then amplifies and phase inverts the sound and feeds the resulting anti-noise to an earphone that applies the antinoise, which arrives with the acoustic noise to be canceled, to the interior or the earcup. While this system is analog, and is therefor fast operating, is an open loop control system, and is not adaptive. The performance of the device is influenced by changes in coupling of the ambient noise to the ear (e.g., by changes in the fit of the device, by head movement), by relative movements of the components, and by the stability of the electronic components. Moreover it operates using vacuum tubes, and so cannot be practically operated on batteries. Further, due to its size, it is not portable.

To overcome these problems, practitioners have advanced the state of the art using closed loop feedforward digital control systems. A simplified view of such a system is shown in FIG. 1. A sound $u_k$ which is to be controlled passes along a duct 1, and is detected by a microphone 3 from which the signal is passed to a control system 5. An electroacoustic transducer 7 is located downstream of the microphone 3, which injects sound into the pipe, in accordance with a control signal applied by control system 5, e.g., in intensity, frequency and phase such as to cancel the sound $u_k$, resulting in the sound $ur_k$, which desirably can be null.

A microphone 9 in the duct downstream from the transducer 7 closes the loop by detecting any residual sound following the cancellation, and returns an error signal to the control system 5, which responds by modifying the control signal applied to transducer 7 so as to minimize $ur_k$ detected at microphone 9.

It will be recognized that the control system 5, operating in the digital mode, has a limitation in speed based on the inherent operating speed of its processor and due to the sampling rate of the primary signal from microphone 3, the error signal from microphone 9 and the control signal provided to the electroacoustic transducer 7. Consequently in practical systems this approach has been limited to applications, wherein the microphone can be placed far upstream of transducer 7, in order to be able to sample the arriving signal as early as possible and thus compensate for the inherent time delay within a digital system.

Due to the above-described speed limitation, this system has not been able to be adapted to the control of random noise entering an earcup without substantial loss in peformance, since microphone 3 is required to be close to the outside boundary of the earcup, and therefore there is insufficient processing time available for the control system to properly control the sound in the earcup.

SUMMARY OF THE INVENTION

Embodiments of the present invention provide means and methods for utilizing a feedforward digital control system in applications in which the difference in time of arrival of sound at microphones 3 and 9 is small, such as an earcup sound control apparatus, with substantial sound control. Key aspects of the invention substantially overcome the inherent time delay within the control system and reduce the processing load of the control system, thus allowing it to generate a practical anti-noise control signal for an earcup type system.

In accordance with an embodiment of the invention, a method of noise control of an acoustic signal is comprised of obtaining a reference signal of the acoustic signal to be controlled, applying an antinoise signal to the acoustic signal so as to control the acoustic signal, obtaining an error signal resulting from the application of the antinoise signal to the acoustic signal, generating said antinoise signal from said reference signal by passing the reference signal through a first filter having controllable filter coefficients, using a simplified model of a signal path from a location of the antinoise signal to a location of the error signal to obtain a modified representation of the reference signal, controlling the first filter coefficients by processing the error signal and the modified representation of the reference signal and generating a coefficient control signal such as to generate the antinoise signal, and applying the coefficient control signal to the first filter.

In accordance with another embodiment, a method of noise control of an acoustic signal is comprised of obtaining a reference signal of the acoustic signal to be controlled, applying an antinoise signal to the acoustic signal so as to control the acoustic signal, obtaining an error signal resulting from the application of the antinoise signal to the acoustic signal, generating the antinoise signal from the reference signal by passing the reference signal through a first filter having controllable first filter coefficients, controlling the filter coefficients by processing the error signal and a modified representation of the reference signal and generating a coefficient control signal such as to generate the antinoise signal, applying the coefficient control signal to the first filter, oversampling at least one of the reference signal and error signal at a rate of at least five times the highest frequency of the acoustic signal to be controlled and updating the first filter coefficients by processing only a time spaced fraction of the oversampled samples of the reference or error signals.

In accordance with another embodiment, the impulse response model of the signal path from a location of the antinoise signal to a location of the error signal is synthesized.

In accordance with another embodiment, at least one of the reference signal and error signal are oversampled at a rate of at least five times the maximum frequency to be controlled, and the antinoise signal is applied to the acoustic signal at the oversampled rate. However the antinoise signal is processed at a rate which is a fraction of the oversampling rate.

Other embodiments of the invention will become clear from reading the description below.

BRIEF INTRODUCTION TO THE DRAWINGS

A better understanding of the invention will be obtained by considering the detailed description below, with reference to the following drawings, in which:

FIG. 1 is a simplified schematic diagram of a prior art type of feedforward noise control system, FIG. 2 is a sectional view of an earcup type of noise control system which can be used in conjunction with the present invention, FIG. 3 is a reproduction of a computer simulation of an adaptive sound controller from the prior art, FIG. 4 is a block diagram of an embodiment of the present invention, FIGS. 5A and 5B illustrate a complete error path impulse response model as in the prior art, and a simplified error path impulse response model as in an embodiment of the present invention, respectively, FIG. 6 is a graph illustrating noise reduction without, and with a simplified error model in accordance with an embodiment of the invention, FIG. 7 is a block diagram of a more detailed structural embodiment of the invention, FIG. 8 is a timing chart used to describe another embodiment of the present invention, FIG. 9 is a schematic diagram of a low order high pass filter that can be used in an embodiment of the present invention, FIG. 10 illustrates an acoustic filter, in accordance with an embodiment of the invention, FIG. 11 is a schematic diagram of fixed-ratio gain amplifiers in accordance with another embodiment of the invention, and FIG. 12 is a graph showing the error path frequency response for the earcup device having an impulse response shown in FIG. 5B, and as measured when the earcup is poorly sealed to the head.

DETAILED DESCRIPTION OF THE PREFERRED EMBODIMENTS

Figure 2:
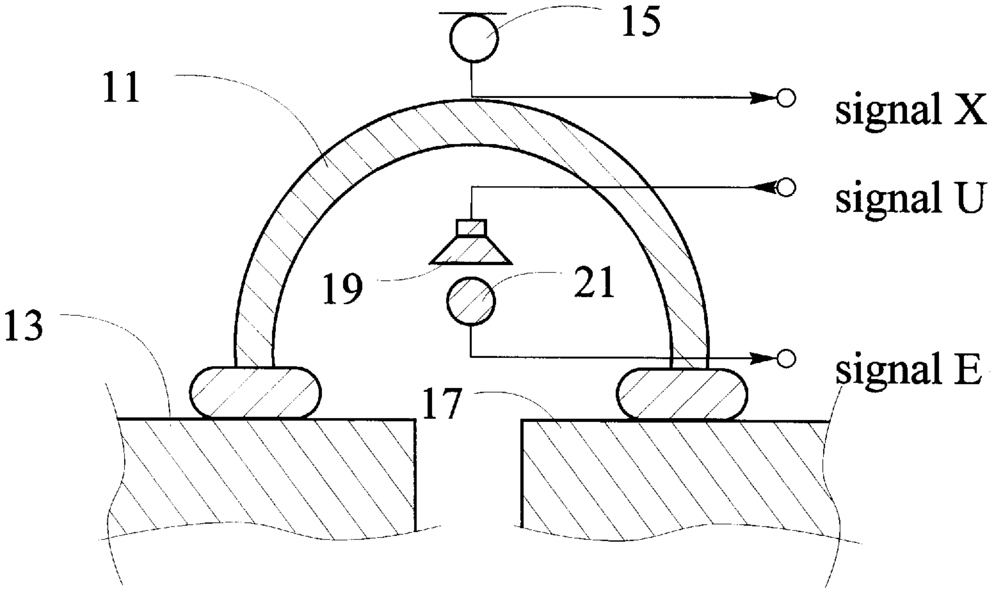

Turning to FIG. 2, an earcup type of sound control system is shown. A sound attenuating earcup 11 is fitted over the ear 13 of a user, and seals to the skin of the user. A reference microphone 15 is located just outside of the earcup, e.g. on an axis with the ear canal 17 of the user.

An electroacoustic transducer (earphone 19) is located within the volume between the earcup 11 and the ear 13, also preferably on the axis with the ear canal and microphone 15. An error microphone 21 is also located in the volume between the earcup 11 and the ear 13, also preferably on the aforenoted axis.

Figure 1:
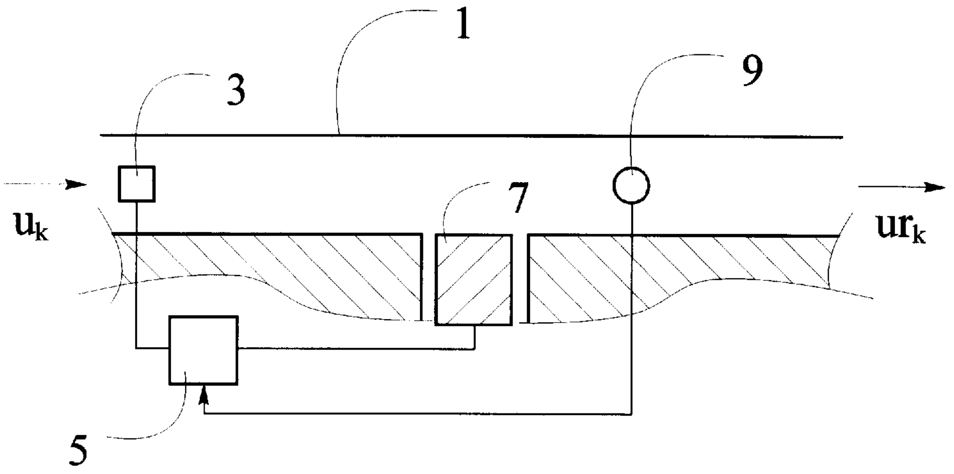
Fig. 1 (Prior Art)

The microphone 15 corresponds to microphone 3 in FIG. 1, the earphone 19 corresponds to the transducer 7 of FIG. 1, and the microphone 21 corresponds to the microphone 9 of FIG. 1. However, it will be recognized that due to the earcup structure (which typically may be in the form of ear protectors/earphones of a helicopter pilot), the microphones 15 and 21 are very close to the earphone 19, allowing little processing time in the control system due to the very short time that it takes for sound to traverse these short distances, and it being not practical to move microphone 15 a significant distance from the earcup.

The article "Active Adaptive Sound Control In A Duct: A Computer Simulation", by J. C. Burgess, in the Journal of The Acoustical Society Of America, 70(3), September 1981, pp. 715–719, describes a theoretical and computer simulated digital adaptive controller for the system shown schematically in FIG. 1. A schematic of a digital feedforward sound control system described in that article, is reproduced in FIG. 3 herein, from FIG. 6 of the article. A description of its operation is considered redundant herein, as its function will be readily deduced from the aforenoted article as well as from the description of an embodiment of the invention as shown in FIG. 4 below.

Figure 3:
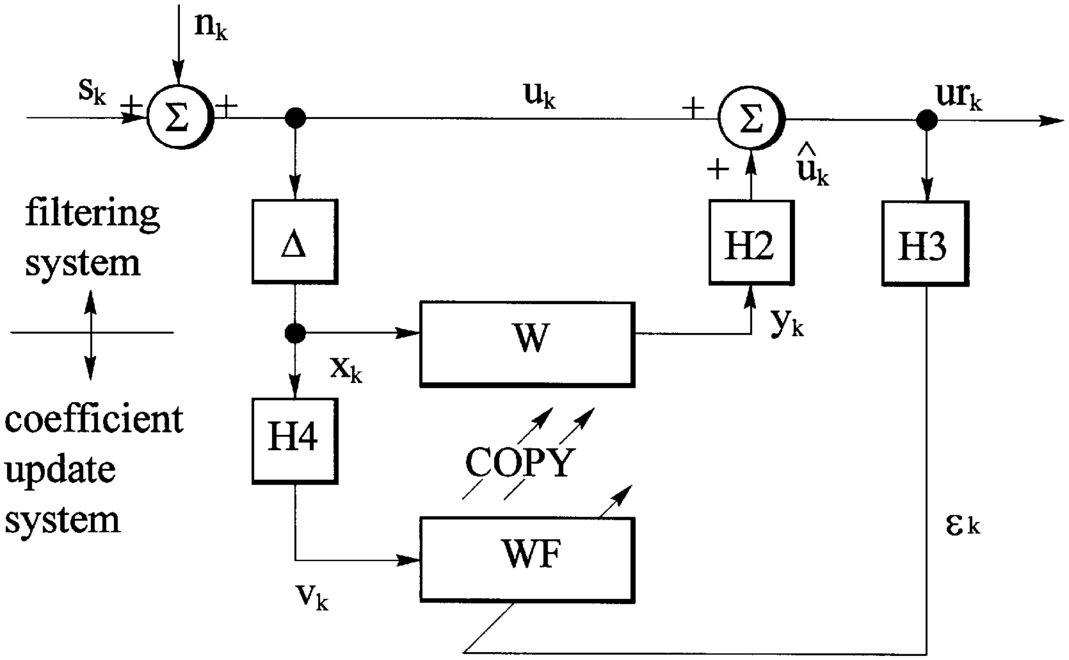
Fig. 3 (Prior Art)
Figure 4:
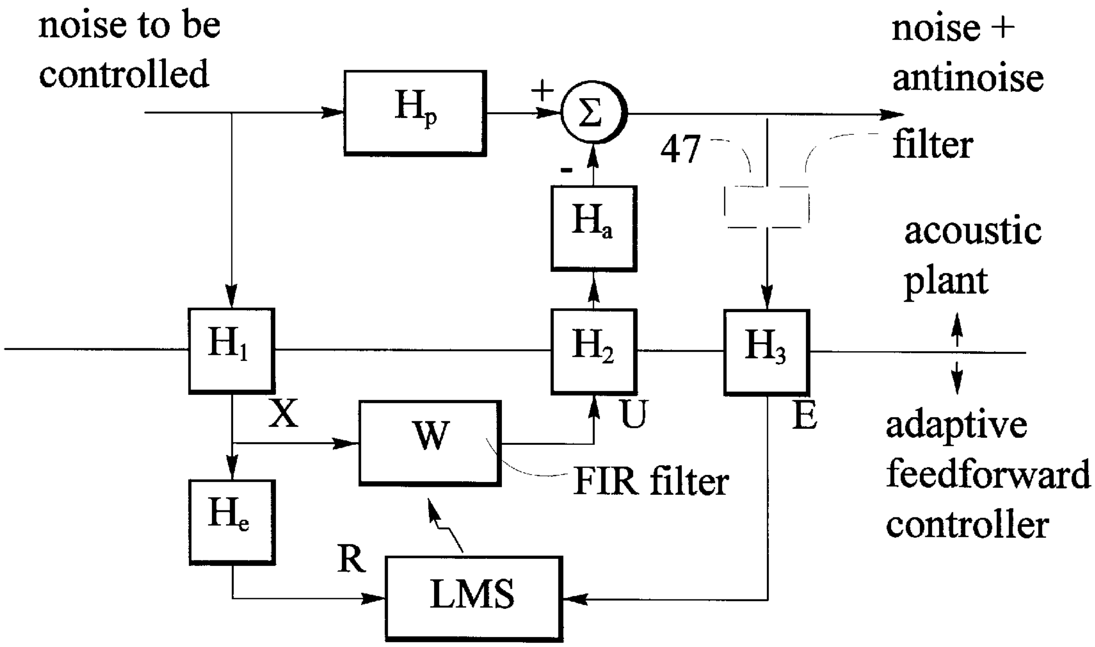

FIG. 4 illustrates an embodiment of the present invention. A transmission path formed by the earcup and cushion against the skin, and air leaks around the cushion, is represented by $H_p$. FIG. 3, by comparison, shows an air conduction path.

In FIG. 4, the transfer function for the digitized signal derived from the sound field outside the ear cup, X, is $H_1$, while that for the error signal, E, is $H_3$. The corresponding function for the secondary source path is $H_2$. The corrective sound pressure generated from signal U experiences a further transmission path in propagating from the earphone to the error microphone, $H_a$.

It may be seen that $H_2$ and $H_3$ have corresponding transfer function blocks in FIG. 3, while the transfer function $H_1$ in FIG. 4 has corresponding element Δ in FIG. 3.

The signal derived from $H_1$ (Δ) is applied to an adaptive FIR filter W, which applies an antinoise signal via transfer function $H_2$ to a summer Σ, to which the acoustic signal to be controlled is also applied. In the system of FIG. 3, the summer is actually the cavity in front of and in the region of the transducer 7 within the duct 1, while in the system of FIG. 4, the summer is the region within the cup 11 particularly between the earphone 19 and the ear canal 17. Here the antinoise signal from $H_2$ output from FIR filter W, passing via transfer functions $H_2$ (and $H_a$ in FIG. 4), is added to the acoustic signal so as to cancel it.

The coefficients of the filter W are controlled by control system WF (FIG. 3), or control system LMS (FIG. 4). These control systems obtain the error signal from transfer function $H_3$, represented by E in FIG. 4 and $\epsilon_k$ in FIG. 3, as well as a reference signal R (FIG. 4) or $v_k$ (FIG. 3). This reference signal is derived by a modification of the sampled reference signal from microphone 3 (FIG. 1), using transfer function $H_4$ in FIG. 3, which forms an error model of the system.

The error model in the prior art system (FIG. 3) is derived from continuous sampling of the system signals, and is a characteristic of the system. The control system WF, after an error model has been determined, varies the coefficients of the adaptive FIR filter W so as to cause an output signal to be applied to the summer to control the sound which is detected at the error microphone 9.

Figure 5A:
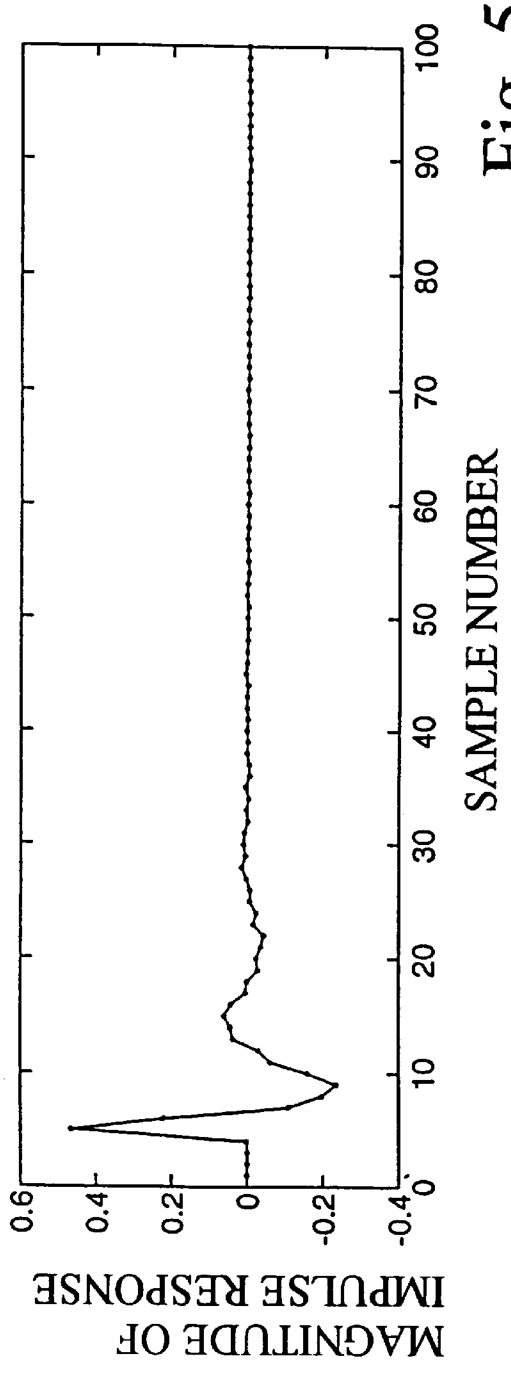
Fig. 5A (Prior Art)

A representation of the error path impulse response model of the prior art system of FIG. 3 is illustrated in FIG. 5A, wherein each dot on the graph represents a different sampling time (the horizontal axis representing the time sequence of consecutive samples). Each point is required to be calculated by a processor in control system W, in order to obtain system identification (characterization). Due to the computational load on the control system processor, it has been found that it is impractical to operate a digital feed-forward active noise control system wherein there is little time between the reference sound pickup (microphone 15), the cancellation sound (earphone 19), and the error sound pickup (microphone 21), as noted earlier.

In accordance with an embodiment of the present invention the impulse response model $H_e$ is synthesized so that it eliminates the need for system identification. In a preferred embodiment of the model $H_e$, the magnitudes of the FIF filter coefficients, $h_i$, satisfy the condition:

$$\sum_{i=1}^{N} h_i = 0 \quad (1)$$

where $i = 1, 2, 3, \ldots N$, and $N$ is the total number of filter coefficients.

Figure 5B:
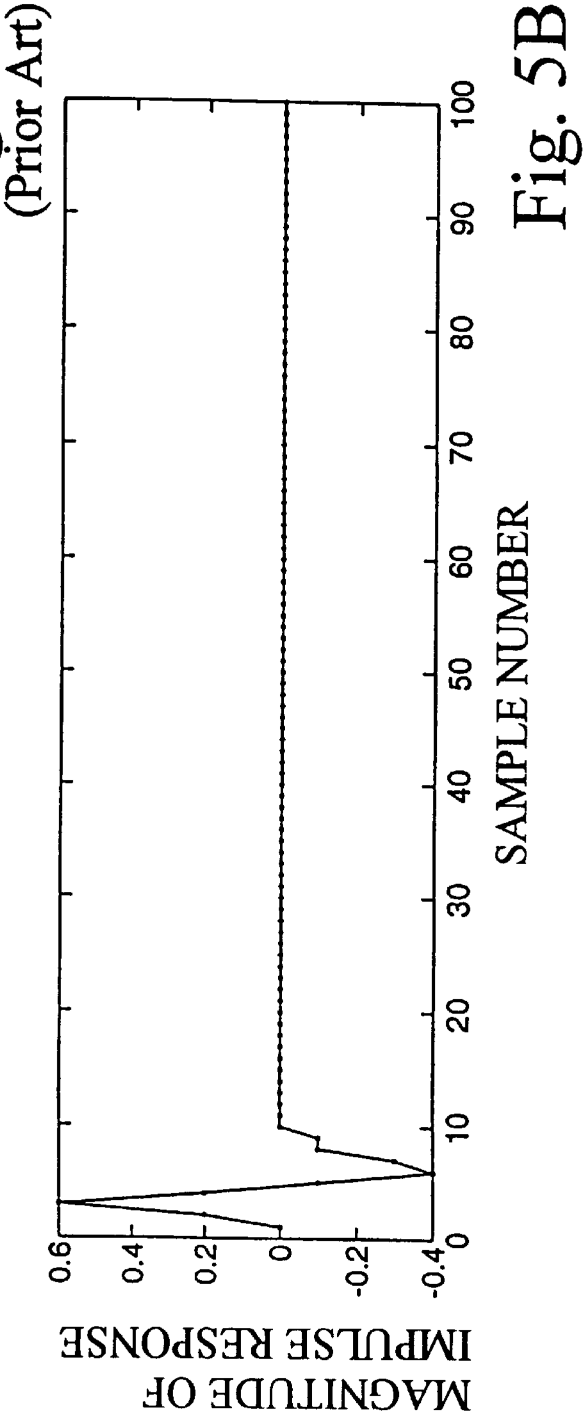

A synthesized impulse model in which this condition is satisfied is illustrated in FIG. 5B. It may be seen (by counting the sampling points) that there are 9 computational points after which all $h_i$=0. Thus in this example N may be set to 9. From the time that the model reaches 0, the computational load on the system processor approaches zero. Compare this with the prior art system of FIG. 5A in which there are 100 non-zero computational points of which about 34 are visibly non-zero points, which represents a significant load on the processor, since a value for R (the response) has to be obtained for each recalculation of the control filter coefficients.

Figure 6:
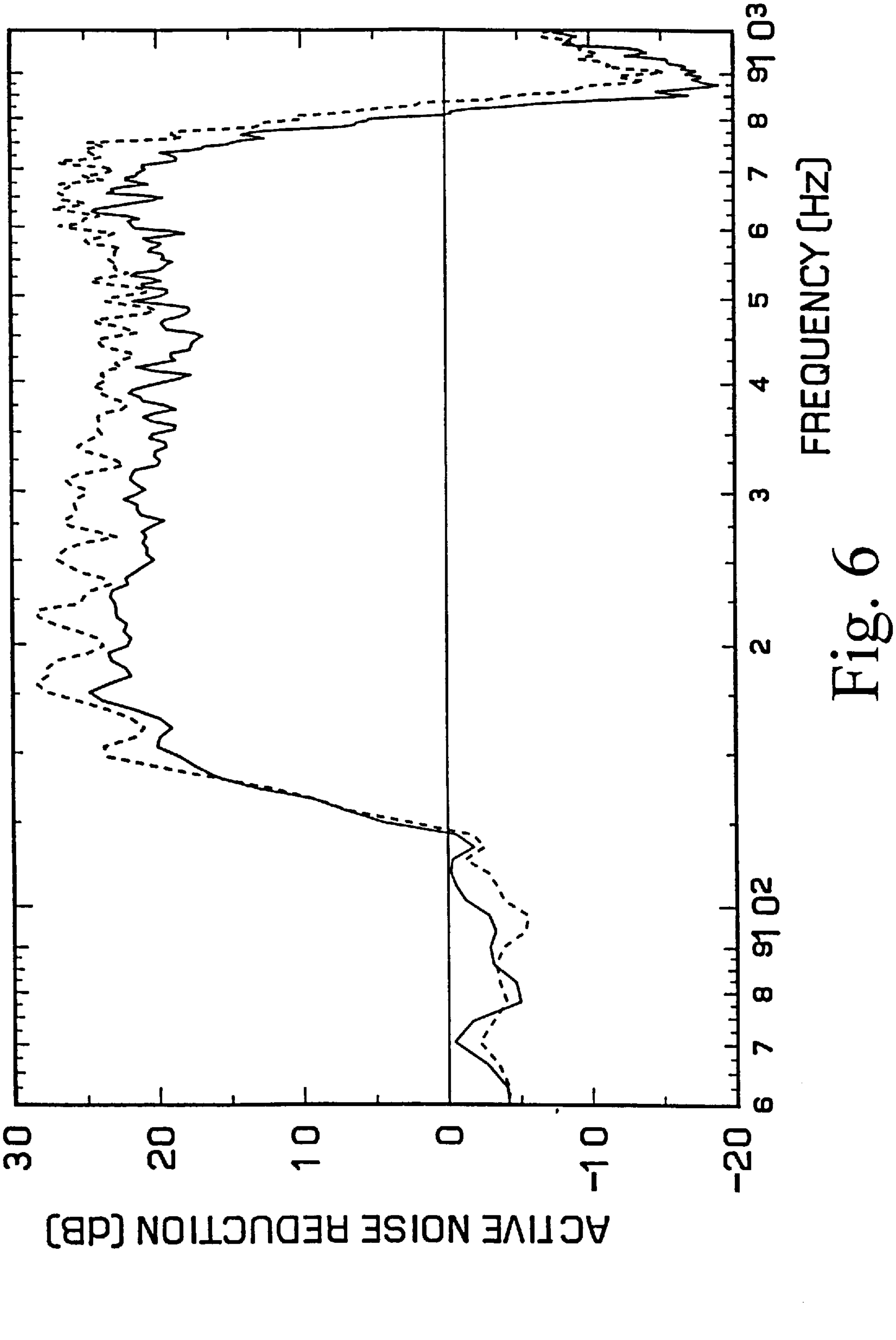

FIG. 6 illustrates the measured active noise reduction of band-limited white noise using a 200 tap FIR filter W using a true error path model with 200 coefficients $h_i$ (the dashed graph) as in the prior art, as compared with the simplified error model with 9 coefficients $h_i$ satisfying equation (1) that is N=9, as in the present invention (the solid line). It may be seen that there is little difference in noise reduction between that obtained with the true error path model and the simplified error path model.

Instead of a synthesized error-path impulse response model used for $H_e$, a truncated measured impulse response model, or a truncated synthesized impulse response model could be used.

Due to the fact that the coefficients of the error path impulse response average and rapidly converge to zero, it is clear that the processing load is significantly decreased. This allows more time for other calculations to be performed during a given time period.

Figure 7:
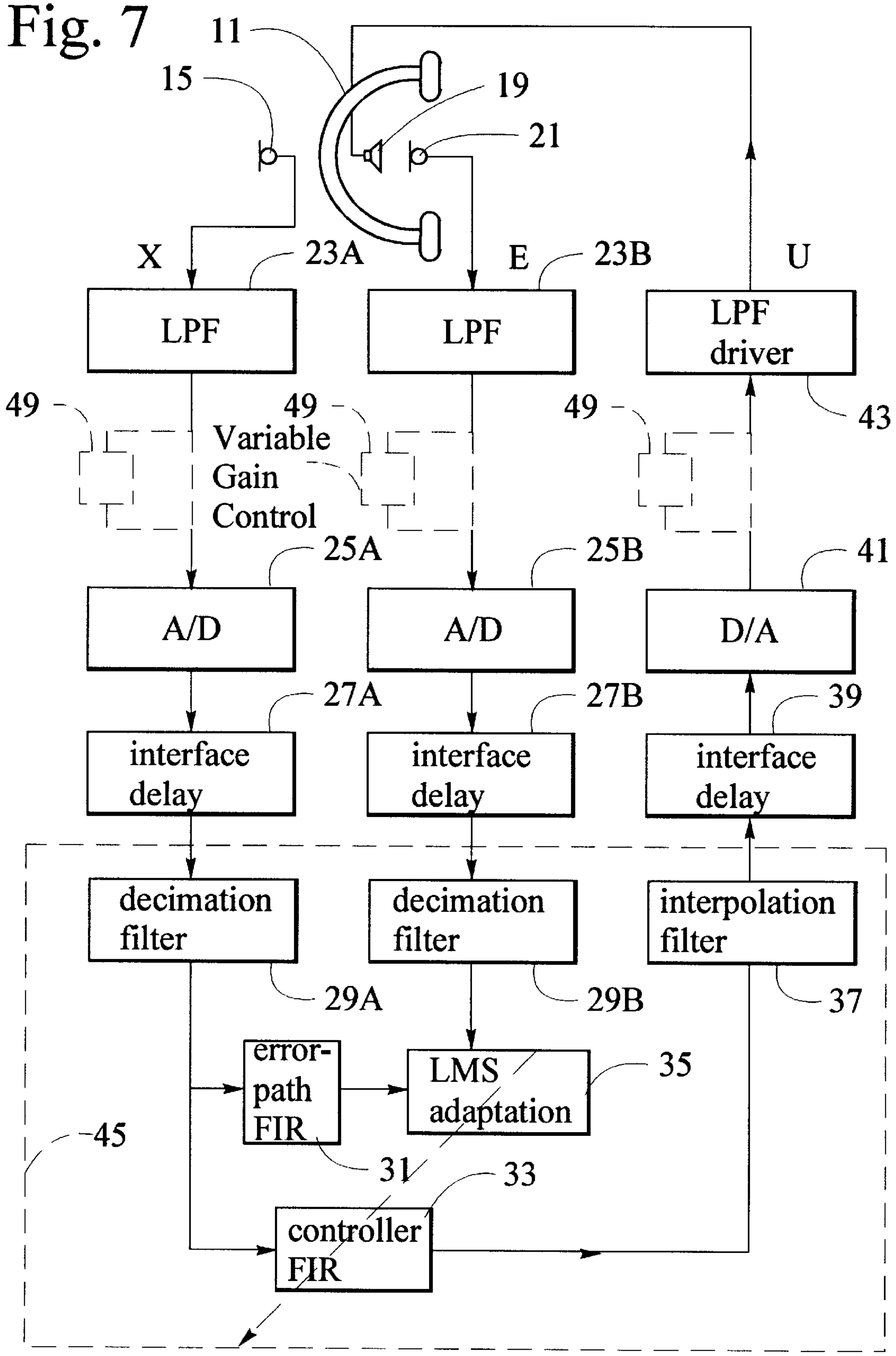

Apparatus to implement the present invention is illustrated in FIG. 7. The elements of the cup system shown in FIG. 2 are reproduced.

The outputs X and E of the microphones 15 and 21 respectively are applied to low pass filters 23A and 23B respectively, in which the bandwidth is limited to low frequencies, which are the frequencies most likely to penetrate the ear cup. The outputs of the filters are applied to A/D converters 25A and 25B respectively, in which the analog signals are converted to digital signals.

The output signals of A/D converters 25A and 25B are subjected to an interface delay 27A and 27B, and from the interface delays the signals are filtered in decimation filters 29A and 29B. The interface delays 27A, 27B and 39 are dependent on the hardware implementations of the active noise control system, which is taken to include any phase delay in the low pass filters 23A, 23B and 43, and is commonly related to the sampling time interval.

The filtered signal from the reference microphone is then applied to error path FIR filter 31 and to controller FIR 33, while the filtered signal from the error microphone is applied to LMS control filter adapter 35.

Error path FIR filter 31 corresponds to and provides the transfer function $H_e$ in FIG. 4, and LMS adapter 35 corresponds to the LMS adapter in FIG. 4. Controller FIR 33 in FIG. 7 corresponds to FIR filter W in FIG. 4, which in a successful embodiment was a 200 tap FIR filter, controlled by LMS adapter 35.

The output signal of filter 33 is applied to an interpolation filter 37, after which the signal is subjected to an interface delay 39. The signal is then converted to analog form in D/A converter 41, and the resulting analog signal is applied to low pass filter and earphone driver 43. The canceling or otherwise acoustic modifying signal from driver 43 is applied to earphone 19.

It is preferred that the decimation and interpolation filters, error path FIR filter, controller FIR filter and LMS controller should all be implemented in a digital signal processor, such as 32 bit floating point type TMS320C31 manufactured by Texas Instruments Inc., illustrated in FIG. 7 as block 45 contained within the dashed line.

The synthesized simplified error path impulse response model is implemented in error path FIR 31, to provide a filtered signal to the adapter 35. The LMS controller algorithm can follow what is described in the aforenoted article by Burgess or algorithms for feedforward control described in "Active Noise Control:Algorithms and DSP Implementations" by S. M. Kuo and D. R. Morgan, Wiley, N.Y., 1996.

It is preferred that the signals from either or both of the microphones should be digitally oversampled. Thus instead of sampling at twice the highest noise frequency to be controlled, it is preferred to sample at a frequency or at frequencies that are equal to or greater than five times this frequency. This process usually reduces the interface time delay, especially when the low-pass filters 23A, 23B and 43 are readjusted to the higher Nyquist frequency.

Figure 8:
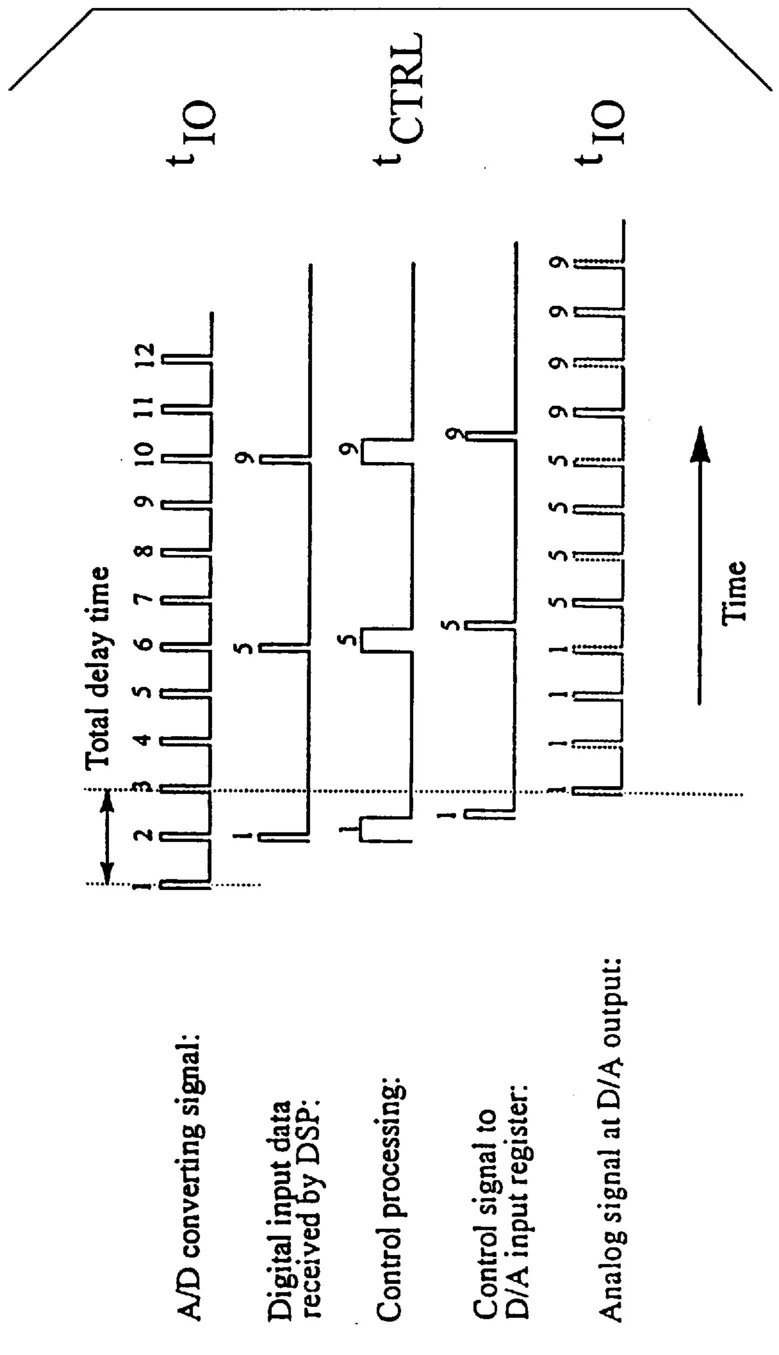

Reference is now made to FIG. 8, which illustrates timing, using the oversampling and decimation filters 29A and 29B. The signal in the top graph shows sampling intervals of the A/D converters 25A and 25B. The frequency of sampling is at the oversampling rate described above, $t_{IO}$.

At the time delayed from the first shown sampling instance, the resulting digital signal is received by the digital signal processor 45, as illustrated in the second row of FIG. 8. It has been found that not all of the sampled data need be processed; the input data from time spaced samples can be processed, and the second row of FIG. 8 illustrates every fourth sample being processed.

The third row in FIG. 8 illustrates that the processing time for each sample passed to the DSP 45 is less than one sampling interval at the control system sampling rate, $t_{CTRL}$. However it should also be noted that there is substantial time between the completion of processing of a sample and the initiation of processing of the next. That time can be used to process another channel (e.g. for a second ear cup), put to other purposes such as processing additional samples, employing control filters with a larger number of filter coefficients, or the DSP can remain substantially idle to reduce electrical power consumption.

At any given sampling rate, an increase in the total number of control filter coefficients permits lower frequencies of noise to be controlled.

As shown in the fourth row, following the completion of processing, the correction (antinoise) signal for the earphone

19 is passed to the D/A converter. The same digital correction signal is applied to the earphone at the oversampled rate until the correction signal changes, at which time a changed correction signal (e.g., corresponding to the fifth, or ninth, oversampled reference input signal) will be applied to the earphone.

The total time delay between sampling the input signal and the production of the correction signal may be seen to be only two oversampling delay time intervals, which is a substantial decrease from the time if the oversampling and decimation method is not used. This allows the reference microphone 15 to be placed close to the earcup, i.e. close to the earphone 19, and makes a practical earcup noise canceling system possible.

In a successful embodiment, the oversampling frequency was 40 kHz, and the control frequency, that is, resulting from the processing of a fraction of the oversampled samples, was 10 kHz (i.e., every fourth sample was processed). The noise bandwidth was 150–800 Hz.

Figure 9:
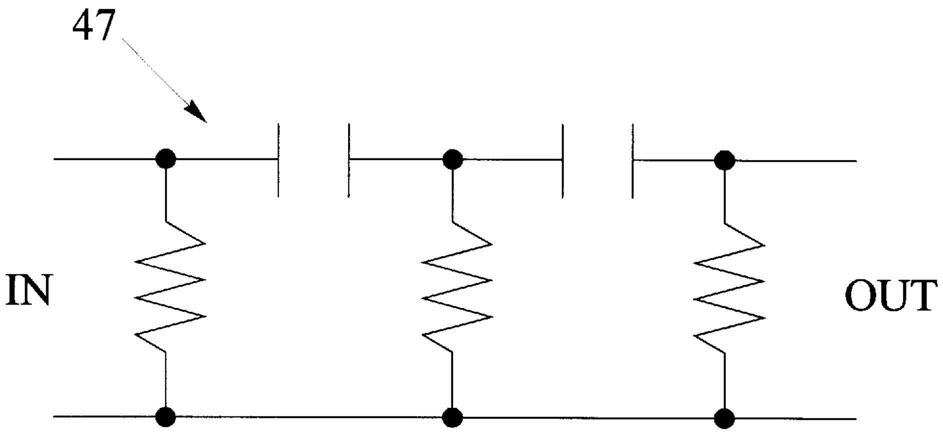

The error and/or reference and/or control signals can be filtered by means of electrical, acoustical and/or electroacoustic filters, as part of transfer functions $H_3$, $H_1$ and $H_2$. Such a filter is illustrated in FIG. 4 as filter 47 in the error signal path, and it is preferred to be a low order analog filter (i.e. a filter with amplitude changing with frequency of no more than 12 db/octave), for example the high pass filter shown in FIG. 9. The example electrical filter 47 shown is comprised of a pair of capacitors in series with one conductor and resistors connected across the pair of conductors between the capacitors and across the input and output. Electrical and acoustical filters of this type are well known and their operation need not be described further herein.

Filter 47 acts to reduce the system response at frequencies at which noise reduction is not required. Band limiting can result in improved noise reduction performance at frequencies at which control is required, reduced power and performance requirements of the secondary acoustic source (earphone 19), and consequent simplification of hardware.

Filter 47 and filters 23A, 23B and 23C permit spectrum shaping of the reference and/or error signals to satisfy predetermined performance requirements, such as psychoacoustic detection criteria or physiological injury criteria.

Figure 10:
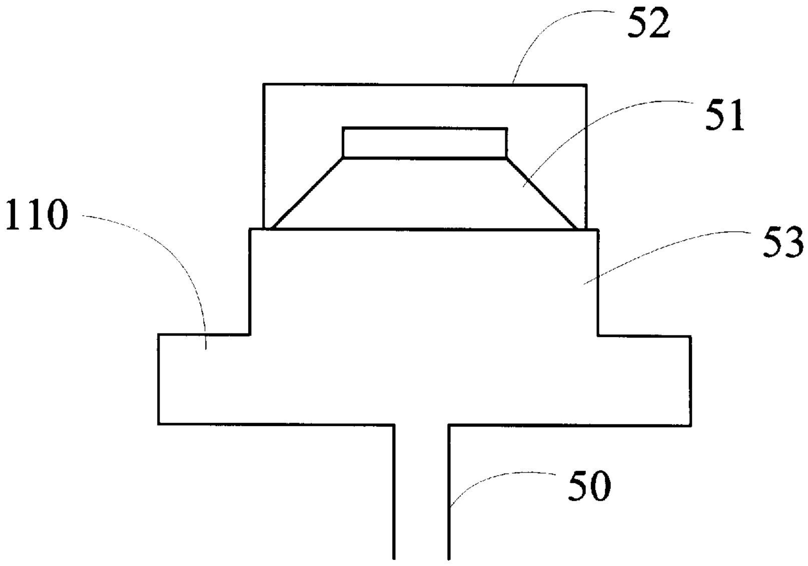

With digital oversampling of the signals from one or both microphones, the low pass filters 23A, 23B and 43 may be replaced by low-order acoustical or electrical filters to simplify further the device. An example of a low-order, low-pass acoustical filter applied to the earphone 19 within an earcup is shown in FIG. 10, as cavity 110 containing exit port 50 (e.g. a small tube) in front of the ear channel 17, coupled to loudspeaker 51 or the equivalent contained in a loudspeaker enclosure 52 via a larger diameter tube 53, being similar in diameter to the active surface of the loudspeaker (the microphones 15 and 21 not being illustrated).

It is also preferred to extend the dynamic range of the reference and secondary acoustic sources in such a way that the error path impulse response remains unchanged, or the error path impulse response and the ratio of the electronic or electroacoustic gains of the reference and error microphones remain unchanged. This can be realized by specialized electronic circuits that simultaneously adjust the electronic amplification of signals X, U and E such that the product of the electronic amplification of signals E and U remains constant, or the product of the electronic amplification of signals E and U, and the ratio X/E remain constant.

To provide the above, as shown in FIG. 7, variable fixed-ratio gain amplifiers 49 can be inserted between the low pass filters 23A and/or 23B, and the following A/D converters 25A and/or 25B respectively, and a variable reciprocal gain amplifier between D/A converter 41 and low pass filter/driver 43. In FIG. 7, the dashed lines represent a bypass of the straight through conduction path otherwise shown to accommodate amplifiers 49. A similar structure is inserted in the other conduction paths as noted above.

Figure 11:
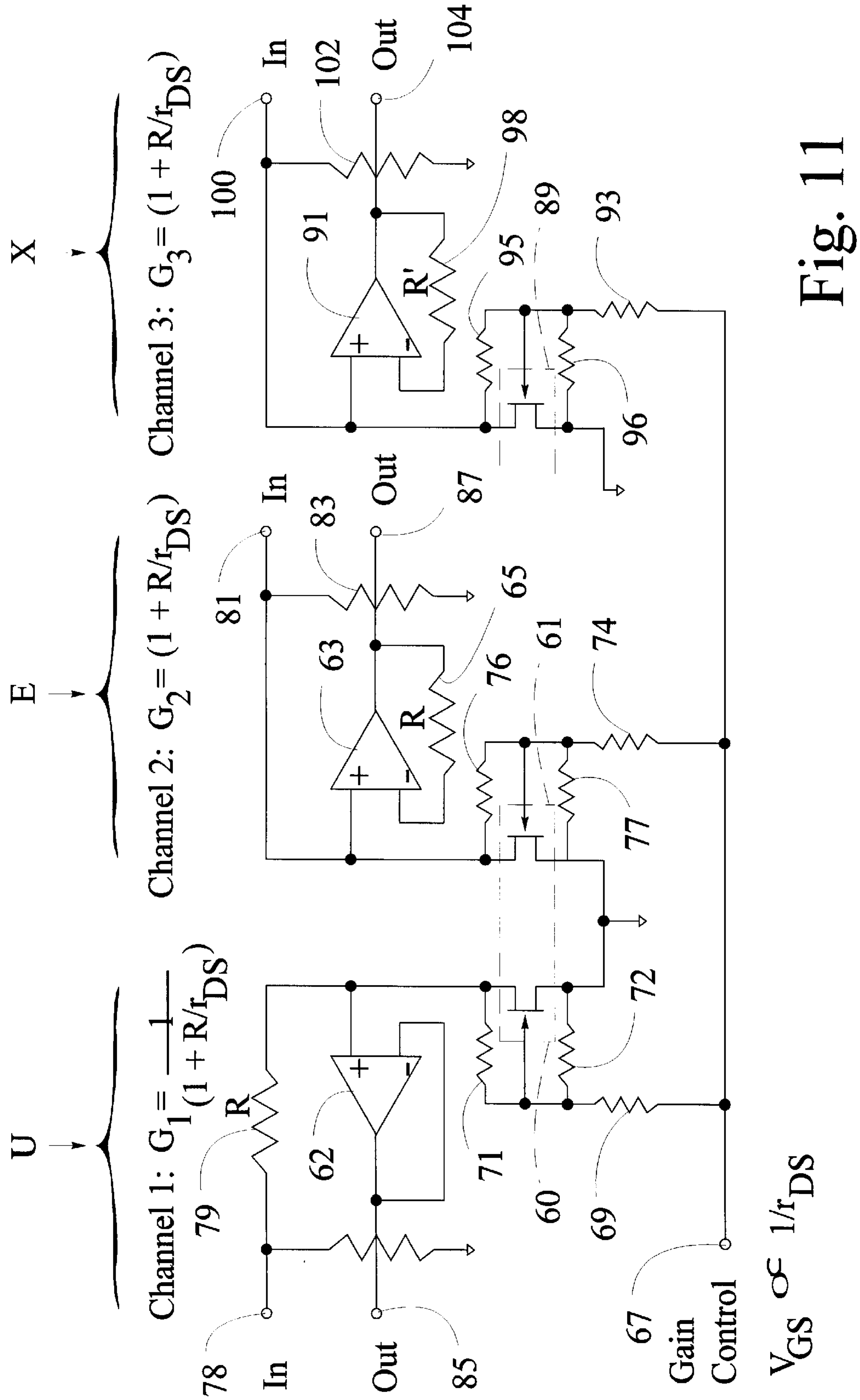

A variable, reciprocal gain and fixed-ratio gain arrangement can be made by means of linear amplifiers having automatic gain control signal paths, as for example channels 1, 2 and 3 illustrated in FIG. 11.

The circuit can be implemented as shown in FIG. 11 by matched field effect transistors (FETs) 60 and 61 having their source drain circuits respectively connected between ground and, for FET 60, the non-inverting input of operational amplifier 62, and for FET 61, the inverting input of operational amplifier 63. The inverting input of amplifier 62 is connected to its output and the non-inverting input of amplifier 63 is connected to the output through a resistor 65, which has a value R.

The gate of FET 60 is connected to a gain control input 67 via resistor 69, and to its source and drain via resistors 71 and 72. Similarly, the gate of FET 61 is connected to gain control input 67 via resistor 74 and to its source and drain via resistors 76 and 77.

The noninverting input of amplifier 62 is connected to input terminal 78, called channel 1, carrying the U-signal, via resistor 79, which has similar value as resistor 65. Terminal 78 is connected to ground via a resistor 80. The noninverting input of amplifier 63 is connected to an input terminal 81, called channel 2, carrying the E signal, and to ground via resistor 83. Output terminals 85 and 87 carry the output signals of channels 1 and 2 respectively.

The amplifier circuit for channel 3, carrying the X signal, is similar to that of channel 2, except for the value of the feedback resistor around the operational amplifier. An FET 89 which is matched to FETs 60 and 61 has its source-drain circuit connected between ground and the inverting input of an operational amplifier 91. The gate of FET 89 is connected via resistor 93 to gain control input 67, and to its source and drain via resistors 95 and 96. Feedback resistor 98, which has a value R', is connected between the output of amplifier 91 and its inverting input.

The input 100 for channel 3, carrying the signal X, is connected to the non-inverting input of amplifier 91, and to ground through resistor 102.

The output of the amplifier 91 is connected to output terminal 104.

Variable gain is provided by matched FETs to obtain the same value of $r_{ds}$. Reciprocal gain amplifiers are obtained by choosing circuit values so that the gain of channel 1 (e.g. carrying the U-signal) is $$G_1 = \frac{1}{(1 + R/r_{DS})} \quad (2)$$

and channel 2 (e.g. carrying the E signal).

$$G_2=(1+R/r_{DS}) \quad (3)$$

A fixed ratio between the gains of channels 2 and 3 (the latter e.g. carrying the X signal) is obtained by using circuit values so that $$G_3=(1+R'/r_{DS}) \quad (4)$$

Figure 12:
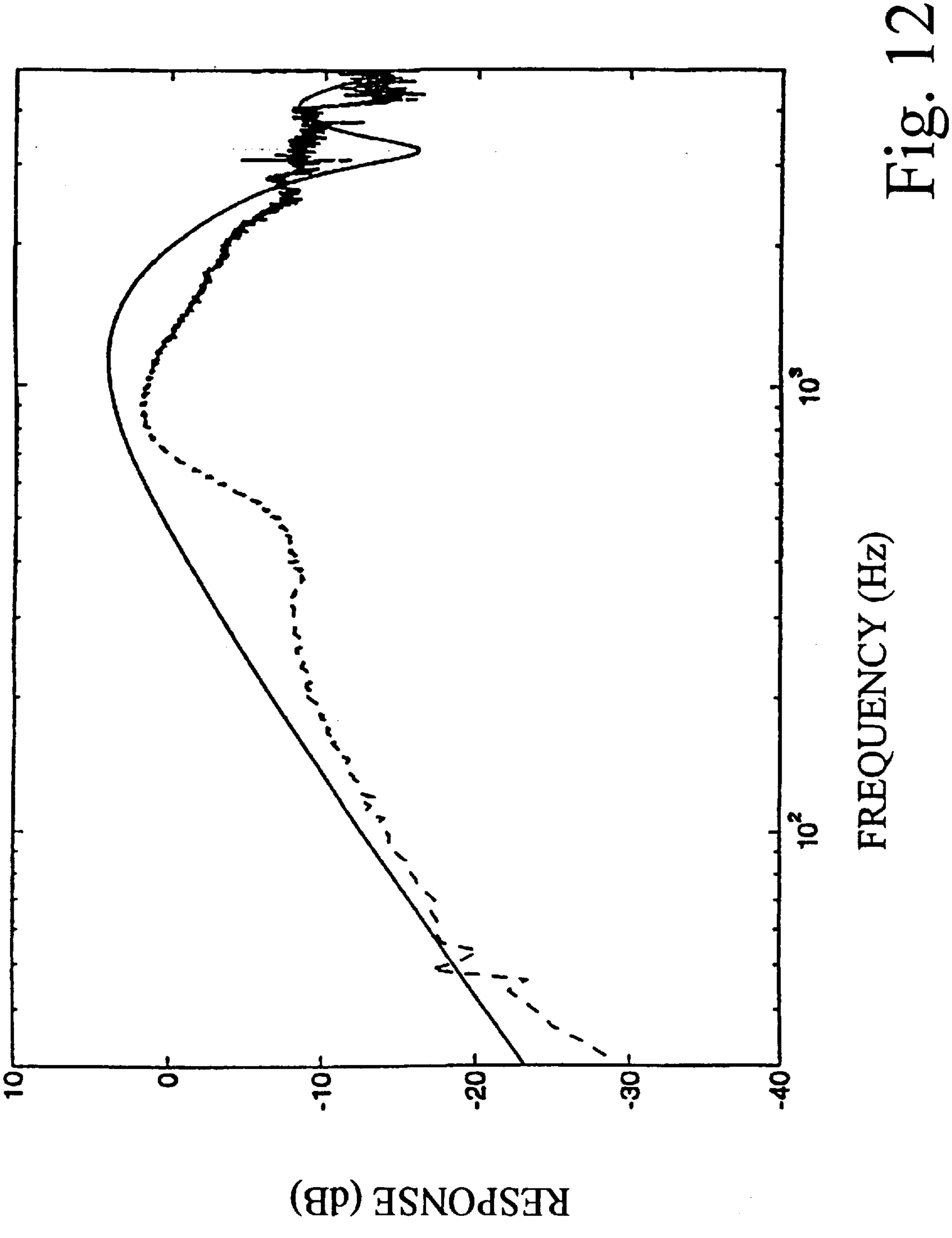

A laboratory prototype of the above-described invention has also demonstrated that it adapts to new conditions, such as when the seal between the cushion of the earcup is broken, as could occur when the user turns his head. This results from the use of a synthesized error path model, designed according to equation (1), in which an air leak comparable to that occurring during poor fit of an earcup on the ear has been included. For example, the frequency response of the synthesized error path model with impulse response shown in FIG. 5B is given by the solid line in FIG. 12. A measured error path frequency response for the same device when the earcup is poorly sealed to the head is shown by the dashed line in FIG. 12.

A person understanding this invention may now conceive of alternative structures and embodiments or variations of the above. All those which fall within the scope of the claims appended hereto are considered to be part of the present invention.

We claim:

1. A method of noise control of an acoustic signal comprising:

(a) obtaining a reference signal of the acoustic signal to be controlled, (b) applying an antinoise signal to the acoustic signal so as to control the acoustic signal, (c) obtaining an error signal resulting from the application of the antinoise signal to the acoustic signal, (d) generating said antinoise signal from said reference signal by passing the reference signal through a first filter having controllable filter coefficients, (e) using a FIR model of a signal path from a location of the antinoise signal to a location of the error signal to obtain a modified representation of the reference signal, in which model the filter coefficients $h_i$ satisfy the condition $$\sum_{i-1}^{N} h_i = 0$$

where i=1, 2, 3, . . . N, and N is the total number of filter coefficients, (f) controlling the first filter coefficients by processing the error signal and the modified representation of the reference signal and generating a coefficient control signal such as to generate the antinoise signal, and (g) applying the coefficient control signal to the first filter.

2. A method as defined in claim 1 in which the impulse response model of the error path is synthesized.

3. A method as defined in claim 1 in which at least one of the reference signal and error signal are oversampled at a rate of at least five times a highest frequency of the acoustic signal to be controlled.

4. A method as defined in claim 3 in which the antinoise signal is applied to the acoustic signal at said oversampled rate.

5. A method as defined in claim 4 including oversampling both the reference and error signals, and including controlling the first filter coefficients by processing only a time spaced fraction of the oversampled samples of the reference and error signals and applying resulting antinoise signals to the acoustic signal at said oversampled rate.

6. A method as defined in claim 1 including low order analog frequency shaping of at least one of the reference signal and the error signal prior to processing and the control signal after processing.

7. A method as defined in claim 6 including low order analog frequency shaping using low-order low-pass acoustical filters.

8. A method as defined in claim 1 including varying the gain of the paths of the reference signal (X), the antinoise signal (U) and the error signal (E) such that the error path impulse response remains unchanged.

9. A method as defined in claim 1 including varying the gain of the paths of the reference signal (X), the antinoise signal (U) and the error signal (E) such that the error path impulse response and the ratio X/E remain unchanged.

10. A method as defined in claim 1 including varying the gain of the paths of the reference signal (X), the antinoise signal (U) and the error signal (E) such that the product of E and U remain constant.

11. A method as defined in claim 1 including varying the gain of the paths of the reference signal (X), the antinoise signal (U) and the error signal (E) such that the product of E and U, and the ratio X/E remain constant.

12. A method of noise control of an acoustic signal comprising:

(a) obtaining a reference signal of the acoustic signal to be controlled, (b) applying an antinoise signal to the acoustic signal so as to control the acoustic signal, (c) obtaining an error signal resulting from the application of the antinoise signal to the acoustic signal, (d) generating said antinoise signal from said reference signal by passing the reference signal through a first filter having controllable filter coefficients, (e) controlling the filter coefficients by processing the error signal and a modified representation of the reference signal and generating a coefficient control signal such as to generate the antinoise signal, (f) applying the coefficient control signal to the first filter, and (g) oversampling the reference and error signals at a sampling frequency of 40 kHz, or lower, and controlling said first filter coefficients by processing only a time-spaced fraction of the oversampled samples of the reference and error signals, said fraction being about one quarter or less, and applying said antinoise signal to the acoustic signal at said sampling frequency.

13. A method as defined in claim 12, including using a simplified model of a signal path from a location of the antinoise signal to a location of the error signal to obtain said modified representation of the reference signal.

14. A method as defined in claim 12 including low order analog frequency shaping of at least one of the reference, the error signal prior to processing, and the control signal after processing.

15. A method as defined in claim 12 including varying gain of paths of the reference signal (X), the antinoise signal (U) and the error signal (E) such that the error path impulse response remains unchanged.

16. A method as defined in claim 12 including varying gain of paths of the reference signal (X), the antinoise signal (U) and the error signal (E) such that the error path impulse response and the ratio X/E remain unchanged.

17. A method as defined in claim 12 including varying gain of paths of the reference signal (X), the antinoise signal (U) and the error signal (E) such that the product of E and U remain constant.

18. A method as defined in claim 12 including varying gain of paths of the reference signal (X), the antinoise signal (U) and the error signal (E) such that the product of E and U, and the ratio X/E remain constant.

19. A method as defined in claim 12 using a FIR model of a signal path from a location of the antinoise signal to a location of the error signal to obtain a modified representation of the reference signal, in which model the filter coefficients $h_i$ satisfy the condition $$\sum_{i-1}^{N} h_i = 0$$

where i=1, 2, 3, . . . N, and N is the total number of filter coefficients.

20. A method as defined in claim 14 including low order analog frequency shaping using low-order low-pass acoustical filters.

21. A method as claimed in claim 1 in which the impulse response model of the error path is truncated.

22. A method of noise control of an acoustic signal comprising:

(a) obtaining a reference signal of the acoustic signal to be controlled, (b) applying an antinoise signal to the acoustic signal so as to control the acoustic signal, (c) obtaining an error signal resulting from the application of the antinoise signal to the acoustic signal, (d) generating said antinoise signal from said reference signal by passing the reference signal through a first filter having controllable filter coefficients, (e) controlling the filter coefficients by processing the error signal and a modified representation of the reference signal and generating a coefficient control signal such as to generate the antinoise signal, (f) applying the coefficient control signal to the first filter, and (g) varying the gains of the paths of the reference signal (X), the antinoise signal (U), and the error signal (E) such that the error path impulse response remains unchanged.

23. A method as defined in claim 22 including varying the gains of the paths of the reference signal (X) and the error signal (E) such that the ratio X/E remains unchanged.

24. A method as defined in claim 22 including varying the gains of the paths of the antinoise signal (U) and the error signal (E) such that the product of E and U remains unchanged.

25. A method as defined in claim 22 including varying the gains of the paths of the reference signal (X), the antinoise signal (U), and the error signal (E) such that the product of E and U, and the ratio X/E remains unchanged.

26. A method as defined in claim 22 including using a simplified model of a signal path from a location of the antinoise signal to a location of the error signal to obtain said modified representation of the reference signal.

27. A method as defined in claim 26 using a FIR model of a signal path from a location of the antinoise signal to a location of the error signal to obtain a modified representation of the reference signal, in which model the filter coefficients $h_i$ satisfy the condition:

$$\sum_{i-1}^{N} h_i = 0$$

where i=1, 2, 3, . . . N, and N is the total number of filter coefficients.

28. A method as defined in claim 22 including low-order analog frequency shaping of at least one of the reference and the error signal prior to processing and the control signal after processing.

29. A method as described in claim 28 including low-order analog frequency shaping using low-order low-pass acoustical filters.

30. A method as defined in claim 22 in which at least one of the reference signal and error signal are oversampled at a rate of five times a highest frequency of the acoustic signal to be controlled.

31. A method as described in claim 30 in which the antinoise signal is applied to the acoustic signal at said oversampled rate.

32. A method as defined in claim 31 including oversampling both the reference and error signals, and including controlling the first filter coefficients by processing only a time spaced fraction of the oversampled samples of the reference and error signals and applying the resulting antinoise signal to the acoustic signal at said oversampled rate.

* * * * *